United States Patent [19]

Saralegui et al.

[11] Patent Number: 5,439,645
[45] Date of Patent: Aug. 8, 1995

[54] APPARATUS FOR AUTOMATICALLY, SELECTIVELY HANDLING MULTIPLE, RANDOMLY ASSOCIATED HEMATOLOGICAL SAMPLES

[75] Inventors: Francisco J. Saralegui, Miami; Alex W. Schlinkmann, Plantation, both of Fla.

[73] Assignee: Coulter Corporation, Miami, Fla.

[21] Appl. No.: 9,190

[22] Filed: Jan. 25, 1993

[51] Int. Cl.[6] .................. B01F 11/00; G01N 35/02
[52] U.S. Cl. ........................... 422/64; 366/128; 366/218; 422/63; 422/67
[58] Field of Search ............... 422/63, 64, 65, 67; 435/312, 316; 366/128, 218

[56] References Cited

U.S. PATENT DOCUMENTS

| | | | |
|---|---|---|---|
| 3,754,444 | 8/1973 | Ure et al. | 422/67 X |
| 4,007,011 | 2/1977 | Greaves et al. | 422/64 X |
| 4,259,289 | 3/1981 | Curry et al. | 422/64 |
| 4,478,095 | 10/1984 | Bradley et al. | 422/67 X |
| 4,544,279 | 10/1985 | Rudolph | 366/132 |
| 4,578,244 | 3/1986 | Cosgrove, Jr. et al. | 422/67 X |
| 4,713,974 | 12/1987 | Stone | 422/64 X |
| 4,844,362 | 7/1989 | Revnivtsev et al. | 241/210 |
| 4,845,025 | 7/1989 | Lary et al. | 435/2 |
| 4,848,917 | 7/1989 | Benin et al. | 366/208 |
| 4,890,930 | 1/1990 | Nohso | 422/63 X |
| 5,005,981 | 4/1991 | Schulte et al. | 366/219 |
| 5,066,135 | 11/1991 | Meyer et al. | 422/64 X |
| 5,110,743 | 5/1992 | Windisch et al. | 422/67 X |
| 5,220,846 | 6/1993 | Niklewski | 366/128 X |
| 5,232,665 | 8/1993 | Burkovich et al. | 422/65 |

FOREIGN PATENT DOCUMENTS 58-80555  5/1983  Japan .

OTHER PUBLICATIONS

Gilson Medical Electronics, Inc., "718 Sampler Manager: A programmer's tool for automatic sample preparation instruments".
Becton Dickinson, "FACSMate TM Sample Introduction System".
WP048 WELLPREP Sample Processor, Operators Manual for Use with Remote Control Wellprep, Apr. 1991.

Primary Examiner—Robert J. Warden
Assistant Examiner—Robert Carpenter
Attorney, Agent, or Firm—Carl Fissell, Jr.; John T. Winburn; Mitchell E. Alter

[57] ABSTRACT

An apparatus which provides an automatic, signal controlled, sample mixing/resuspending, aspiration and delivery system; wherein a demountable, rotatable carousel temporarily holds a multiplicity of sample containers. Electro-mechanical means, including optical sensors, is programmed to automatically move the carousel to a pre-selected position. A self centering vortexer/mixer lifts a selected sample container from the carousel, sealingly engages the sample container within a sample container support and thereafter orbitally mixes and resuspends the sample container contents. An aspiration probe enters the sample container through the support to receive the sample, which is forced out of the sample container by means of compressed air introduced into the sample container via the sample container support. The sample is delivered to an operably associated flow cytometer via the aspiration probe, after which the probe is washed and readied for the next cycle of operation.

13 Claims, 8 Drawing Sheets

APPARATUS FOR AUTOMATICALLY, SELECTIVELY HANDLING MULTIPLE, RANDOMLY ASSOCIATED HEMATOLOGICAL SAMPLES

BACKGROUND OF THE INVENTION

1. Field of the Invention

The present invention relates to apparatus for automatically handling a multiplicity of randomly associated hematological samples, and, more particularly, concerns apparatus for automatically mixing, resuspending and aspirating pre-prepped blood samples and transferring such resuspended samples to other operably associated cytometric apparatus.

2. Description of the Prior Art

U.S. Pat. No. 4,845,025, entitled "Biological Sample Mixing Apparatus and Method" relates to automatic biological sample mixing apparatus for use in flow cytometric apparatus, wherein a sample container is secured loosely at its top by means of a multi-reagent dispensing head; and the container is mounted at its bottom on a resilient support disposed on an elliptically rotatable member, to cause reagents introduced into the container to be thoroughly mixed with a sample in the container in a fast, efficient, gentle, and accurately repeatable manner.

A recent improvement upon the COULTER® Q-Prep and also protected by U.S. Pat. No. 4,845,025 is the COULTER® Multi-Q-Prep which consists of a 32-tube capacity removable carousel, sensor and sequencing devices, a reagent delivery system, mixer and timing devices. An indexing base moves the carousel in counterclockwise direction to a home position and during sequential sample processing. A tube detector/lifter senses the presence of a sample containing tube in the carousel at mixing position and lifts it up into the dispensing head. A retractable dispensing head adds precise amounts of reagents to the sample. A vortexer/mixer mixes reagents into the sample.

Such prior art, while capable of efficiently and accurately mixing various reagents with the sample, requires that the mixed or pre-prepped sample be removed manually from the mixing apparatus (the COULTER Q-Prep or Multi-Q-Prep) and also the tube and transferred manually to a sample analyzer, for example, a flow cytometer such as the COULTER® EPICS® Profile or XL. Both apparatuses utilize pressure syringes to provide fluid movement. The Q-Prep apparatus does not use bar codes or a bar code reader, inasmuch as it operates on a single, operator manually delivered sample container, one at a time. The Multi-Q-Prep carousel has its 32 tube positions bar coded for sample I.D. Also, these two patented apparatuses rotate in one direction only; and one utilizes a cam and lever operated drive and the other has a notched belt for container rotation and reagent mixing. Vacuum devices and pumps, as used in the apparatus, are relatively expensive, require continuous care and maintenance and the cost is sometimes considerable to the point where it might become prohibitive for small laboratories or medical offices.

SUMMARY OF THE INVENTION

The present apparatus avoids the foregoing shortcomings by providing an automatic, motor driven, signal controlled, sample resuspending, aspiration and delivery system wherein a demountable, rotatable carousel is provided for temporarily holding a multiplicity of individual sample containers. Each sample container holds an individual sample and carries a bar code readable indicia for identifying the patient and for other data. The carousel also includes a discrete identifying bar code, as well as a series of individual sample container position identifying bar codes for indicating the location of each sample container disposed on the carousel.

Means are provided for moving the carousel to a pre-selected position and thereafter for removing a single sample container from the carousel and moving the container into sealing contact with an aspirating head probe, while orbitally rotating the selected sample container so as to mix and resuspend the container contents. Air pressure providing means, secured to the sample tube support head, forces air under pressure through the head into the selected sample container, forcing the container contents, or a portion thereof, out of the container through the sample aspirating probe and into means interconnecting the sample head with operably associated flow cytometry devices or equipment. Means for flushing and washing the sample aspirating probe also is incorporated in the sample tube support head.

The present apparatus also includes a high efficiency, high speed bar code reader, for reading the coded indicia on each sample container as well as for reading the carousel position code and the position code of each sample container on the carousel. Electronic control circuitry operably associated with this apparatus enables all operations to be performed in a fail-safe manner, such that tube jams, tube breakage or absence of tubes from the carousel can be noted, identified by position and action taken to avoid stoppage, breakdown or personnel injury. The present apparatus is completely enclosed by suitable closure members of metal or plastic, which members can be opened to provide operator access for loading, operation, maintenance, repair, cleaning and/or replacement of parts.

DESCRIPTION OF AN EMBODIMENT OF THE INVENTION

Figure 1:
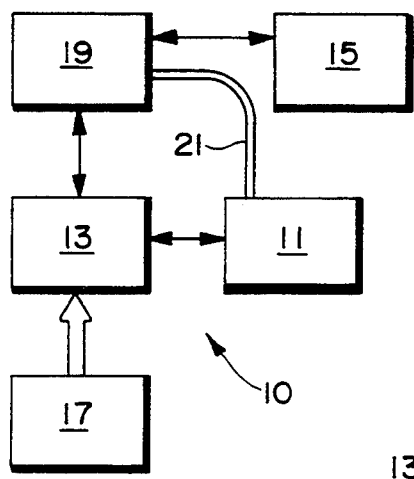
FIG. 1 is a schematic block diagram of the present invention, as used with flow cytometric apparatus.

Apparatus embodying the present invention, as illustrated in the drawings, is adapted to perform in a multifunctional capacity as a completely self-contained, modular unitary assemblage as an operational adjunct to an operably associated flow cytometer, such as the COULTER® XL, Profile or Elite. The present apparatus accomplishes a plurality of related functions, wherein separate structural assemblies are cooperatively combined and integrated into a single, modular, free-standing apparatus 10.

The apparatus 10 can be employed for hematologic sample handling used by a hematology laboratory, researchers and in hospitals. The operation of the apparatus is completely automatic and does not require an attendant technician to monitor its progress or its output results. A laboratory technician can load the apparatus with a sample carrying carousel, start the apparatus and walk away to perform some other laboratory or office function.

As seen in the block diagram of FIG. 1, the modular apparatus 10 comprises four major assemblies: a mechanical assembly 11, an electrical control assembly 13, a work station 15, and a software assembly 17. The assemblies 11–17 can be considered together to provide a Multi-Q-Prep Carousel Loader or MCL. A receptor assemblage 19 can include any flow cytometer, for example, a COULTER® Elite, Profile or the XL, depending on the particular requirements of the user researcher, laboratory or hospital.

Figure 2:
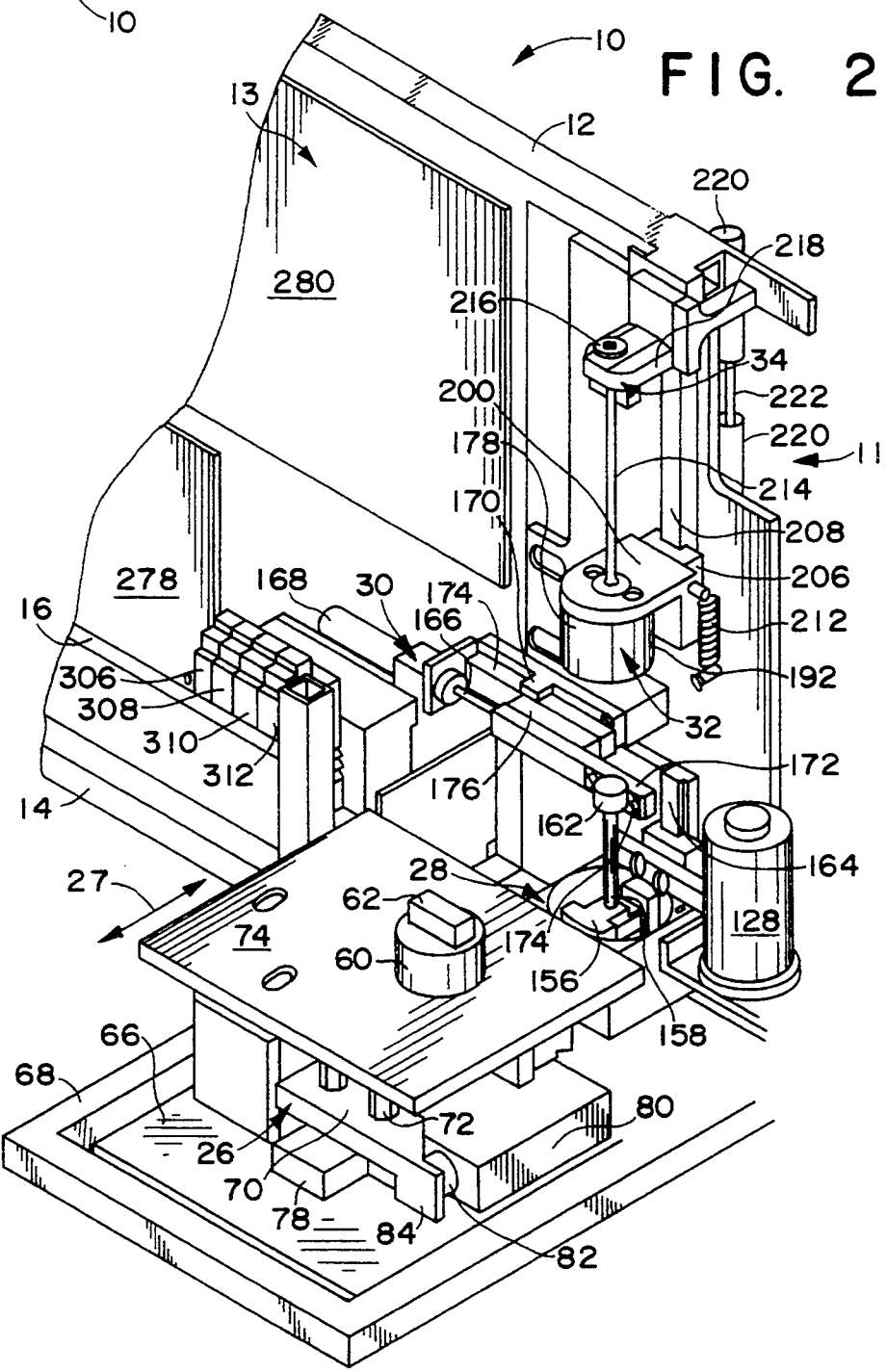
FIG. 2 is an isometric view of apparatus embodying the present invention.

As clearly seen in the isometric view of FIG. 2, the mechanical assembly 11 and the electrical control assembly 13 are structurally combined into the modular apparatus 10, which comprises a plurality of functionally integrated, mechanical and electrical subassemblies. The mechanical assembly includes a vertically disposed support member 12, which is secured at its base 14 to an L-shaped member 16.

The apparatus 10 includes among other things, a sample tube carrying carousel 20 (FIG. 3), having sample tubes 22 thereon. The sample tubes 22 can be standard test tubes of glass or plastic. Also included in the apparatus 10 is a disc-shaped carousel support 24 (shown in dotted outline in FIG. 3); a horizontal slide mechanism 26 (FIG. 2) for moving the carousel 20 and carousel support 24, back and forth in the direction of the two-headed arrow 27 (FIG. 2); a self-centering lifter vortexer/mixer 28, for resuspending the contents of the sample tubes 22, carried by the carousel 20; a pivoted, horizontal, sample tube rotating and steadying member 30; a sample tube support head 32; and a vertically movable sample aspirating member 34.

Located at various fixed positions on the apparatus 10, are a plurality of individual position locating and sensing devices, which will be described in detail with respect to FIG. 8. To the left of the mechanical assembly and operating mechanisms 11 just described are a plurality of electronic control components secured to the vertical support wall 12, making up the electrical control assembly 13 for controlling and directing the automatic operation of the MCL apparatus 10. The electrical control components are disposed on two printed circuit boards 278 and 280.

The operation of the MCL apparatus 10 is completely automatic and can be energized from an operably associated flow cytometer as part of the receptor assemblage 19 (FIG. 1) by way of interconnecting sample delivery tubes 21 and a software processor of the software assembly 17, which can be run on the flow cytometer 19.

Figure 4:
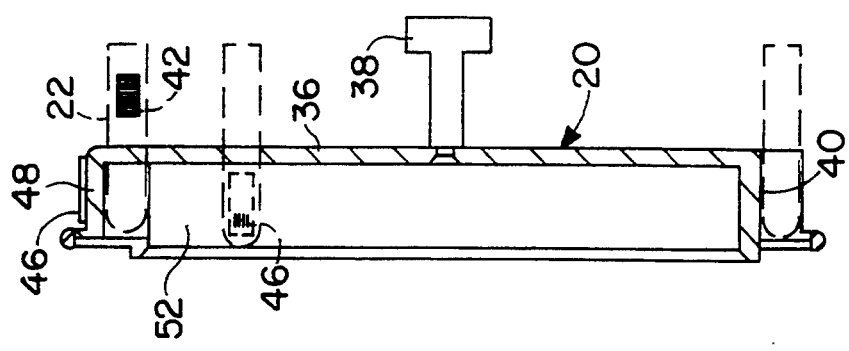
FIG. 4 is a sectional view along line 4—4 of FIG. 3.

The carousel 20 (FIG. 4), for supporting and transporting the sample tubes 22, is constructed as a shallow circular, rigid member 36, provided with a central, vertically projecting handle 38 and a series of thirty-three peripheral, fairly shallow, cylindrical pockets 40, to slidingly receive an individual sample container tube 22. The tubes 22 project upwardly from the respective pockets 40 a sufficient distance to expose an individual bar code indicia label 42 secured around the surface of each tube 22. Each pocket 40 is identified by a position number 44, which is disposed on the upwardly exposed face of the carousel 20. A bar code label 46 also is applied to the rim portion 48 of the carousel 20, at each position corresponding to a pocket on the carousel.

The carousel 20 is demountably mountable onto the circular carousel support member 24 (dotted outline in FIG. 3), which is received within an inner, hollow, cup-shaped area 52 (FIG. 4) of the carousel 20. At a position corresponding to a so-called "home" position, the rim of the support member 24 is provided with an outwardly extending projection 54 (FIG. 3), engagable with and receivable within a matching notch 56 in the carousel 20. The support member 24 is attached to a stub shaft 60, having a horizontal integral rib 62 (FIGS. 2, 3) at its top. The rib 62 receives a matching rib-shaped slot 64 in the bottom center portion of the support member 24.

A base plate 66 (FIG. 2) is disposed on a forwardly extending portion 68 of the mechanical assembly 11 and provides a base for the horizontal slide mechanism 26. The slide mechanism 26 comprises an L-shaped support 70, provided with four pedestal members 72, which support plate 74. The support 70 is slidably mounted on an elongated guide member 78 and is adapted to be moved forwardly and rearwardly double headed arrow 27, by means of a double acting air cylinder 80, a piston shaft 82 of which is connected to a depending tang 84 on the vertical end of the support 70. A forward stop member (not shown), secured to the base member 14, acts to limit the inward travel of the slide mechanism 26.

Figure 5:
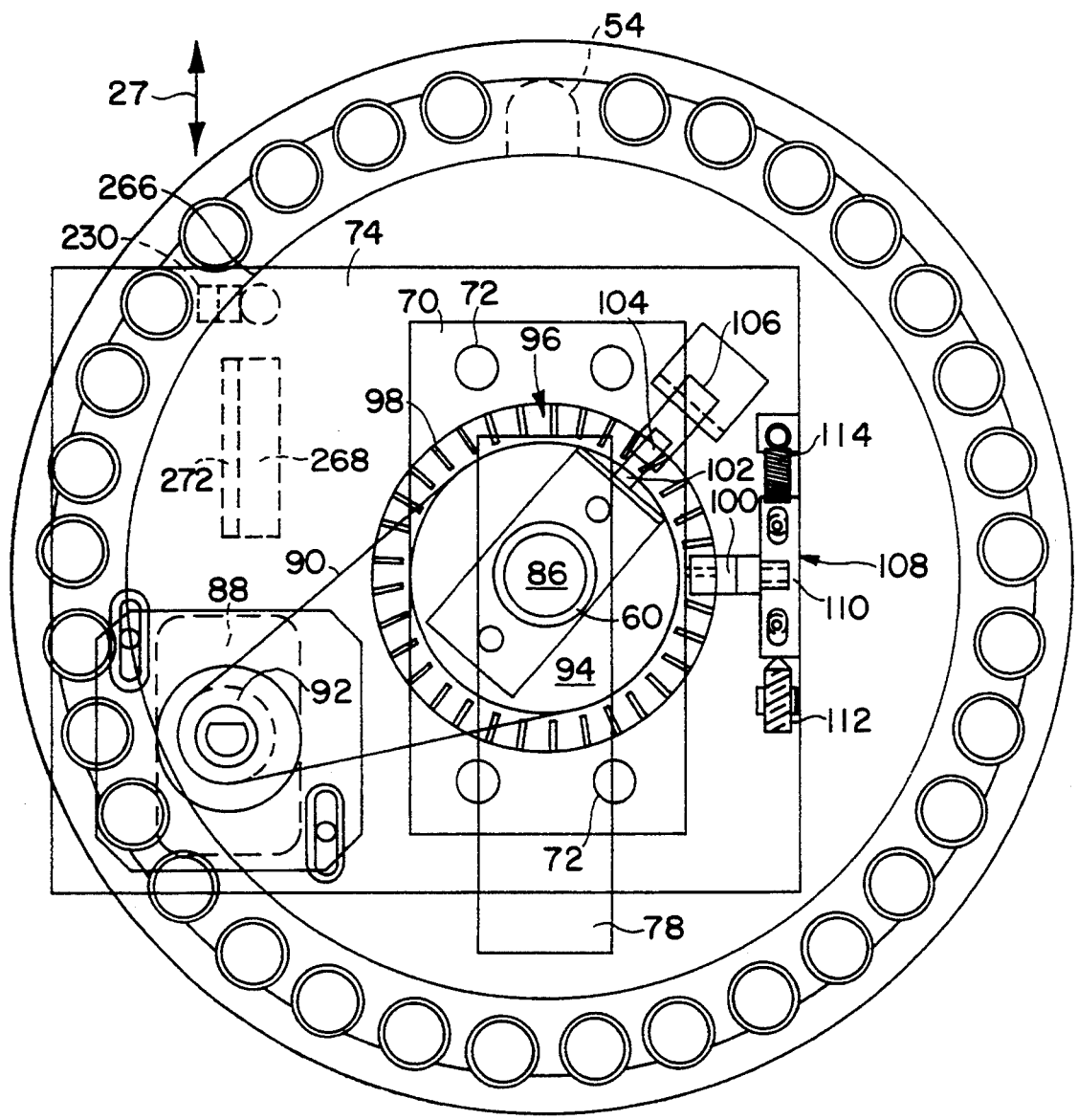
FIG. 5 is an enlarged top plan view of the carousel drive train and operably associated position sensors, although portions of this figure are actually obscured from view by reason of mechanical overlays, the figure is nevertheless illustrated in full rather than dotted line to avoid unnecessary visual confusion.

FIG. 5, as earlier mentioned, is illustrated in full line rather than dotted line, since it is believed that dotted lines detailing one portion of the apparatus obscured by other portions of the apparatus would confuse rather than illuminate the subject matter. The specification clearly and succinctly locates and describes all portions of the apparatus, whether in plain sight or hidden from view. As seen in FIG. 5, the circular stub shaft 60 is secured at its lower end to a drive shaft 86 which extends vertically upwardly through the plate 74. An electric stepper-type drive motor 88 is supported beneath the plate 74. A drive belt 90 extends from a drive pulley 92 on the motor 88 to a driven pulley 94 on the drive shaft 86. An otherwise opaque disk 96 is provided with a plurality of radial, light-passing areas or stripes 98 and is secured to and rotatable with the drive shaft 86.

A sample tube 22 position sensor 100 is secured beneath the plate 74 and includes a yoke or U-shaped sensor which extends outwardly to straddle the perimeter of the disk 96 and permit the disk, when rotated, to interrupt light which is passed between a photodiode on one side thereof to a photoreceptor on the opposite side thereof (neither of which are shown in FIG. 5). A light interrupting member 102 is rotatable with the drive shaft 86 and projects between ends of a U-shaped carousel home position sensor 106, for purposes to be explained.

In order to ensure the accuracy of the centering alignment of each tube 22, an additional adjustment of the MCL apparatus 10 is provided by means of an adjustment member 108, FIG. 5. The tube position sensor 100 is mounted on a slidably movable member 110, slidably secured to the underside of the plate 74. A set screw 112 is provided to move the member 110 horizontally a slight distance against the tension of a spring 114. By adjusting the member 108, the tube position sensor 100 can be moved slightly, so as to position a tube 22 exactly centered under the sample tube support head 32, as well as precisely over the center of the LV mixer 28.

Figure 6:
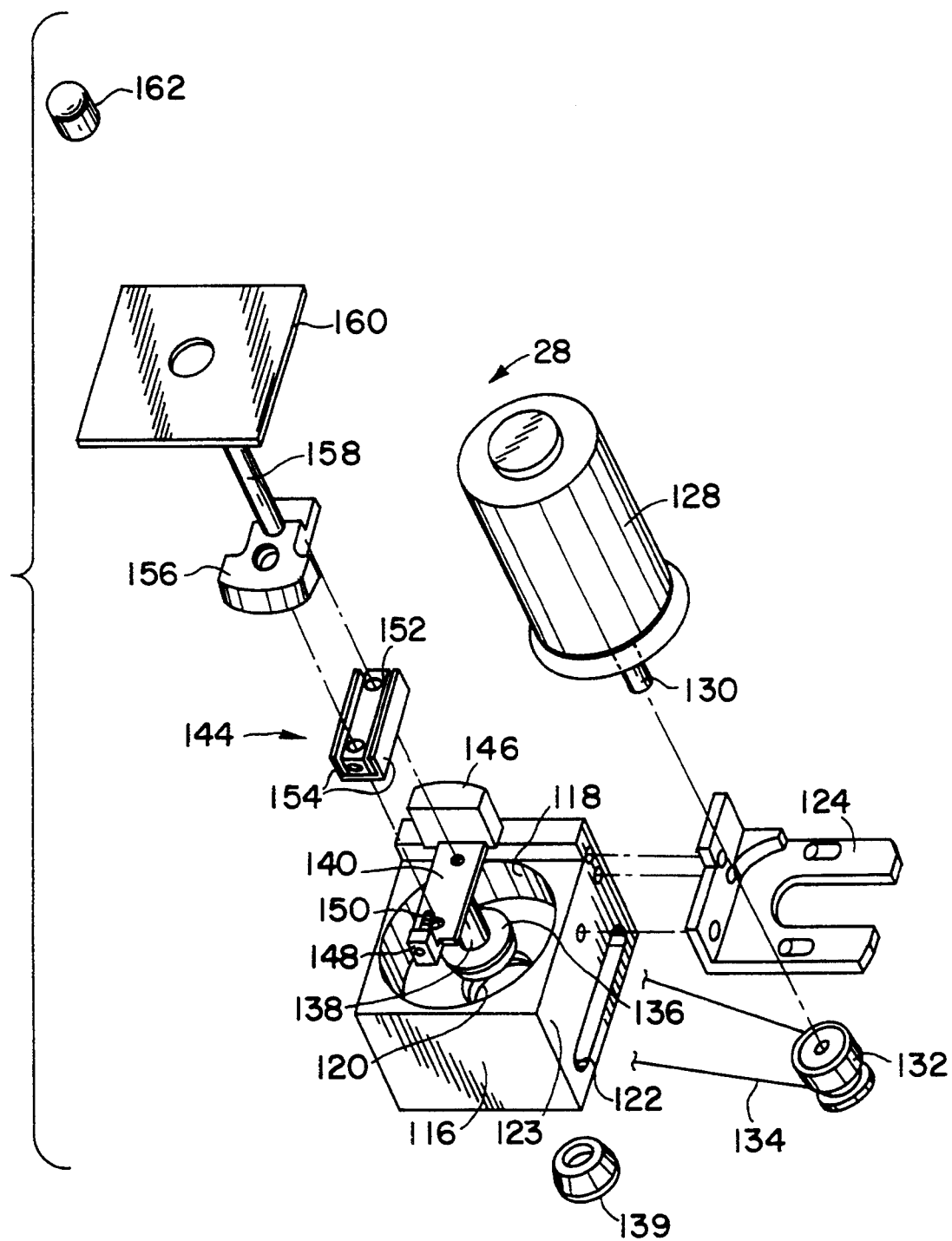
FIG. 6 is an exploded view of the self centering lifter vortexer/mixer for the invention.

Between the carousel support slide mechanism 26 and the rear vertical wall 12 is the self-centering, lifter vortexer/mixer 28. The vortexer/mixer 28, as seen in detail in FIG. 6, comprises a rigid, cube-shaped member 116 having a large, central bore 118, concentric with a smaller bore 120, extending from the top surface of the cube 116 completely therethrough. One side of the cube 116 has an oval-shaped orifice 122 extending from side surface 123 into the central bore 118. An L-shaped bracket 124 is attached to the surface 123 and supports a drive motor 128 having a drive shaft 130 and a drive pulley 132. A drive belt 134 extends from the drive pulley 132 through the lozenge-shaped opening 122 and engages a driven pulley 136 which is mounted on the lower end of a vertically disposed shaft 138. The lower end of shaft 138 is rotatably mounted in a bearing member 139 secured into the bottom of the cube 116. The upper end of the shaft 138 carries a support 140, to which a ball slide 144 is secured. At one end of the support 140 is a small upstanding weight 146; and at the opposite end of the support 140 is a stop block 148, from which a small spring 150 projects toward the weight. The slide 144 has an inner portion 152 which is moveable horizontally between upstanding guide rails 154. A counter weight or imbalance member 156 has a vertically disposed shaft 158 centered thereon. The shaft 158 projects through a cover plate 160 and includes a small, slightly resilient, spherically hollowed knob or button 162 for non-damaging engagement with the bottom of the sample container tubes 22.

In the inactive position, without power being supplied to the drive motor 128, the spring 150, at one end of the ball slide 144, centers and aligns the vertical lifting/erecting shaft 158 with the drive shaft 138. In this aligned position, the spherically hollowed knob or button 162 can be accurately positioned beneath the bottom of a sample tube 22. When power is applied to the drive motor 128, the imbalance weight 156, as a result of the rotative force, causes the shaft 158 to move horizontally outwardly into a circular orbit, creating a vortexing/mixing action with respect to the contents of the tube 22. When the drive motor is turned off, the shaft 158 returns to the center position as a result of the absence of rotative torque; thus automatically self-centering the shafts 138 and 158.

With reference to FIG. 2, the self-centering lifter vortexer/mixer 28 is slidable vertically along a vertical guide 164 which is attached to the vertical wall 12 by means of a guide yoke (not shown) secured to the rear side of the cube-shaped member 116. Vertical movement of the lifter vortexer/mixer 28 is provided by means of the double acting air cylinder 163, the piston shaft 165 of which is connected to the rear portion (not shown) of the cube member 116. This movement of the vortexer/mixer 28 provides translational movement of the individual sample tubes 22, with respect to the tube carrying carousel 20.

Disposed at right angles to the vertical disposition of the lifter vortexer/mixer shaft 158 and at the level of the bottom of a tube 22, when in position, is the tube rotating and steadying member or finger 30. The finger 30 projects horizontally outwardly away from the shaft end 166 of an air cylinder 168. The finger member 30 is pivotally mounted at its center 170 and is attached at one end to the air cylinder shaft 166. The opposite, free end, 172 of the finger 30 is provided with a flexible, shock absorbent pad 174, of rubber or similar resilient material. A double acting air cylinder 176 is secured to the rear of the finger 30 for extending and retracting the finger 30 into and out of the path of movement of the lifter vortexer/mixer shaft 158, during each operation of the MCL apparatus 10.

Figure 7:
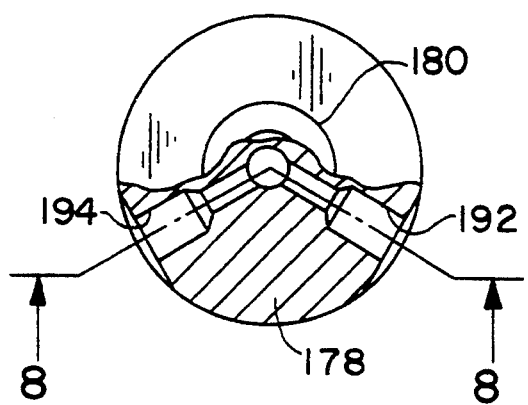
FIG. 7 is a sectional view of the sample tube support head.
Figure 8:
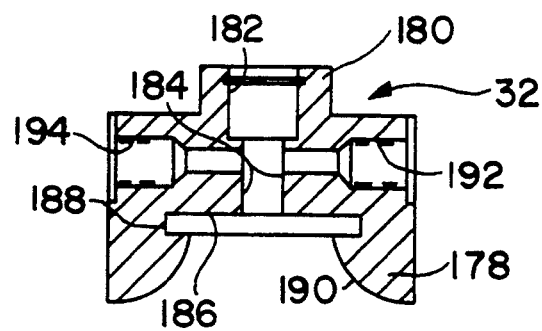
FIG. 8 is a view along the line 8—8 of FIG. 7.

The sample tube support head 32, as illustrated in FIGS. 2, 7 and 8, comprises a cylindrically shaped body 178 and integral concentric attachment member 180 (FIG. 8). A series of concentric bores 182, 184, and 186, extend downwardly within the body, with the outermost bore 186 having an undercut 188. The lowermost portion 190 of the body 178 is outwardly flared. The body 178 further includes outwardly extending, angularly offset, passageways 192 and 194, which open into the central bore 184 and provide means for mounting conduits (not shown). Fluid can be introduced into the passageway 192 to swirl downwardly into a sample tube 22. The passageway 194 is to be coupled to a source of vacuum, which is used to apply vacuum to the sample tube support head 32 to remove any residual fluid remaining after each operation.

The attachment member 180 of the support head 32 is disposed within a circular opening 198 in an L-shaped bracket 200, the rear portion of which is mounted to a slide block 206 (FIG. 2), which is slidable up and down along a guide rail 208, which is secured to the front surface of the wall 12. A coiled spring 212, one end of which is attached to the support head 32 and the opposite end of which is attached to the wall 12, biases the support head 32 upwardly.

The sample aspirating member 34 is employed for directing sample fluid under pressure from the sample tubes 22 into the flow cytometer 19 via the sample delivery tube 21. As shown in FIG. 2, depending from the aspirating member 34 is a probe 214, having a small opening at its lower end. The upper end of the probe 214 is flared outwardly to provide a retaining rim 216 for demountably supporting the probe 214 in a vertically slidable block 218, which acts as a support for the probe 214 and is arranged to be moved up and down along the guide rail 208. An air cylinder 220 has its plunger 222 secured to the slide block 218 for moving the aspirating probe 214 up and down, as called for during apparatus operation.

Figure 9:
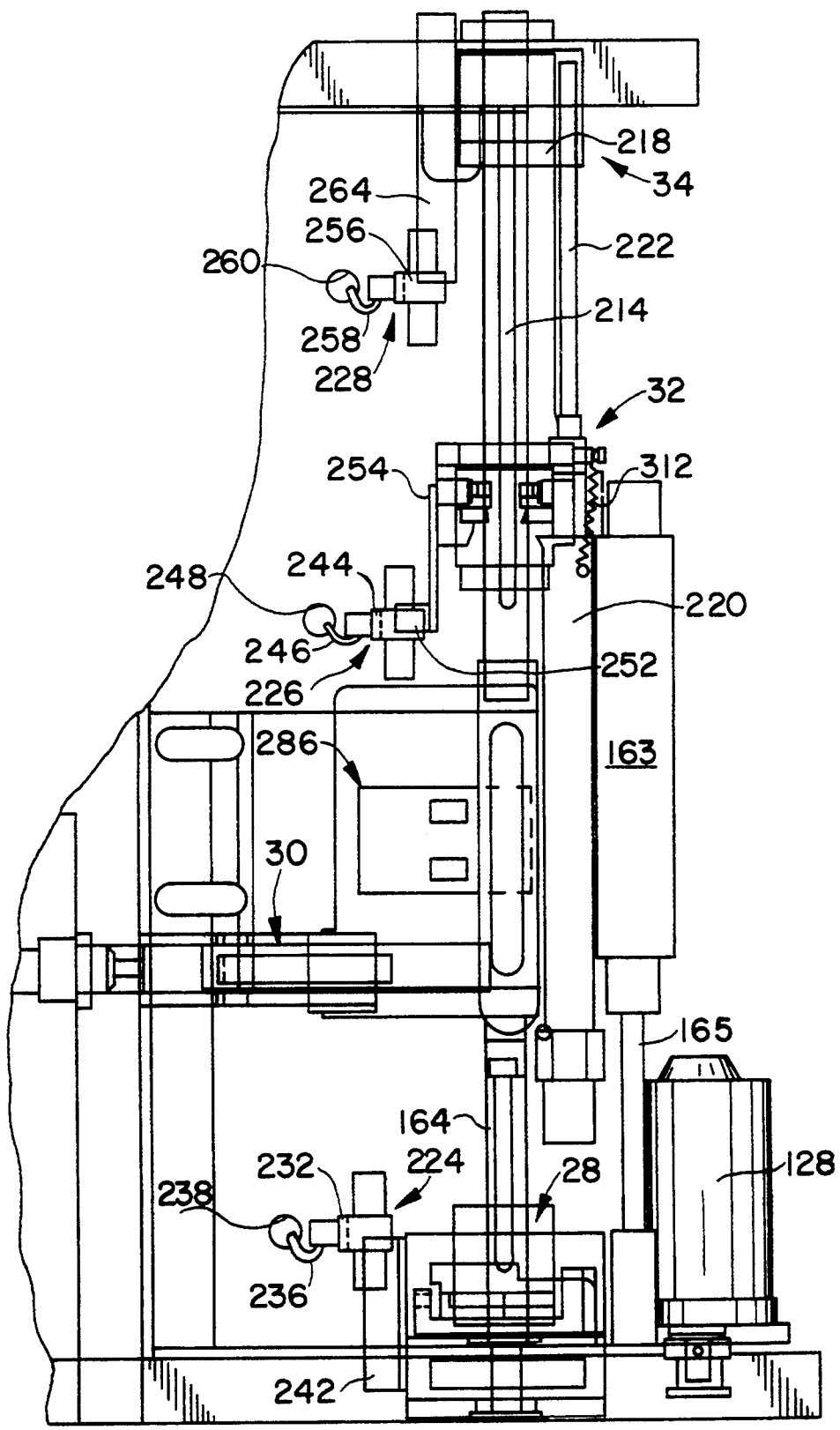
FIG. 9 is a front view of the apparatus of FIG. 2 illustrating various sensing devices used with the present invention.

The MCL apparatus 10 employs a variety of electromechanical sensors which are used to indicate, monitor and cause the adjustment of the status of various of its portions. Not all of these sensors will be described in detail, either because they form part of a specific chip component, or because their operation is thought to be obvious from the general operational description. Four of the sensors are utilized to make the MCL apparatus 10 efficient, simple to operate, failsafe, and automatic with due regard to reliability and safety. As seen in FIG. 9, three of these four sensors (starting at the bottom of the drawing) include an LV mixer up/down detect sensor 224, a sample head detect sensor 226, and a sample probe detect sensor 228. The fourth sensor, a carousel in/out detector 230, will be described later in connection with FIG. 5. All four sensors are substantially identical in construction and operation; although each has an actuator which differs slightly from the others by reason of its separate function.

The LV mixer up/down detect sensor 224 includes a U-shaped sensor body 232, with a photooptical LED on one arm of the U and a photoreceptor on the opposite arm of the U (neither of which are shown in the figure). The sensor body 232 is secured to the support wall 12. Electrical lead wires 236 are arranged to pass from the sensor body 232 through a grommeted aperture 238 in the wall 12 for interconnection to a LV up/down detect chip 240, shown in FIG. 10. An actuator member 242 for the LV up/down mixer sensor 232 comprises a flat, opaque strip of metal or similar material, which is secured to and moves with the LV/vortexer mixer 28. The actuator of each sensor interrupts the light passing from the LED of a sensor to its opposite positioned photoreceptor. An output signal thus produced is used to indicate and control the status, for example, of the LV mixer member 28 via the LV up/down detect chip 240.

The sample head detect sensor 226 includes a U-shaped sensor body 244 which is mounted to the wall 12. Its electrical lead wires 246 pass through a grommeted aperture 248 and are interconnected to a head detect chip 250 on the printed circuit board. An actuator member 252 for the sample head detect sensor 226 comprises an opaque member integral with an elongated attachment member 254 which is secured to the side of the sample tube head support 32.

The sample probe detect sensor 228 has a sensor body 256 and its electrical leads 258 pass through a grommeted opening 260 for connection to a sample probe detect chip 262. Probe actuator 264 is elongated and is attached to the vertically slidable block 218.

Figure 10:
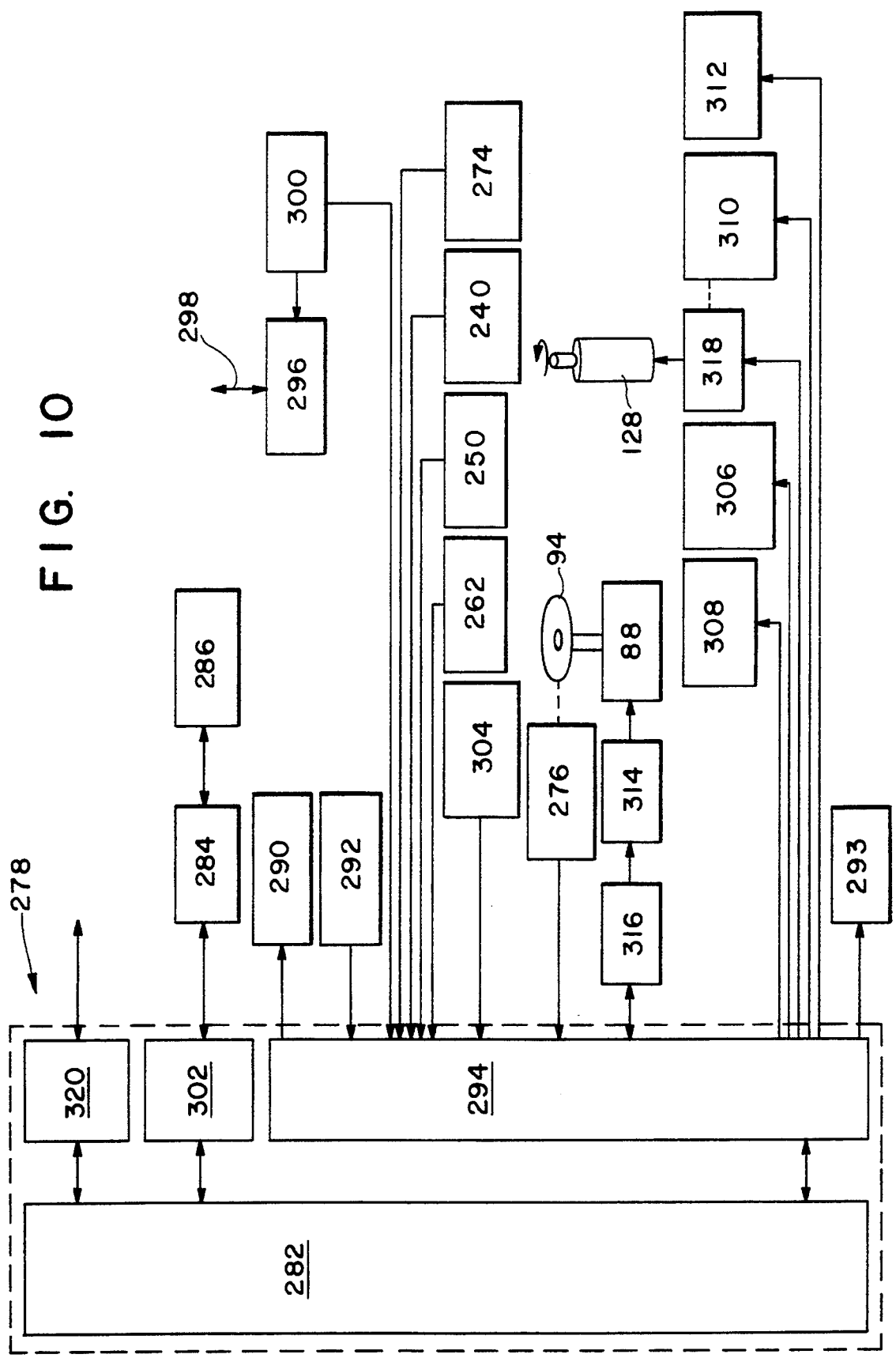
FIGS. 10 and 11 are functional block diagrams of the electrical and electronic control apparatus for the present invention.

The fourth sensor in the group, the carousel in/out detect sensor 230, is located beneath and depends from the slidable carousel plate 74, as shown in FIG. 5. The sensor body 266 forms a gap between two opposing arms of its U-shape. Actuator 268 is secured to the base 66 (FIG. 2) and is L-shaped. An upstanding flange 272 of the actuator 268 is adapted to pass through the gap in the sensor 230 as the carousel 20 is moved in and out in the direction of the two-headed arrow 27. Electrical lead wires (not shown) connect the sensor 230 to the carousel in/out detect chip 274 (FIG. 10).

The operation of carousel sensor 230 is extremely important to the overall operation of the MCL apparatus 10. The sensor 230 indicates to the carousel in/out detect chip 274 the positional status of the carousel. It is essential to the MCL operation that the carousel be correctly positioned with respect to the lifter vortexer/mixer up/down apparatus 28, otherwise the lifter mixer 28 could be actuated prior to a sample carrying tube 22 being in position over the lifting/erecting shaft 158. Incorrect centering of the shaft 158 with respect to the tube 22 could cause the vertical lifting movement of the erecting shaft 158 to break or jam the sample tube, possibly contaminating the entire work area and causing a health hazard, or damage to the apparatus. The carousel in/out detect sensor 230 prevents these problems, The operation of this sensor is substantially identical to that of the other two sensors.

The MCL 10 has two (2) position sensing mechanisms 106 and 100 to determine the location of the carousel 20. One is utilized to place the carousel near the actual "home" position, the other to accurately position the carousel at any of 33 tube positions (including "home").

The stepper motor 88, previously referred to, controlled by the system hardware and software, turns the carousel. Positioning accuracy is approximately 0.15 thousands of an inch. By reading the state of the positioning sensors 106 and 100 and pulsing to the stepper motor 88, the MCL controller 282 can position the carousel to any desired location. The tube position detect sensor 100 and the home position detect sensor 106, are electrically connected to a tube position/home position detect chip 276 (FIG. 10). Both sensors 106 and 100 are shown in FIG. 5 and are substantially identical in construction and operation to that of the other sensors hereinbefore described.

The MCL apparatus 10 has a hinged cover (not shown) for fitting over at least the carousel 20 and the sample tubes 22 to inhibit aerosol from the open top tubes from entering the work area and also to prevent contaminants from falling into the tops of the tubes. The hinged cover activates a switch (not shown) which is coupled to the cover interlock detect chip 304 of the CPU controller 282, such that each time the cover is opened, the computer program in the CPU controller 282 causes the stepper drive motor 88 to rotate the carousel support 24 so that the projection 54 stops at a "load" position. The "load" position is 90° to the left of the "home" position in which the projection 54 is pointed toward the rear of the MCL apparatus 10, as illustrated by the two-headed arrow 27 in FIGS. 2, 3 and 5. When the carousel 20 is placed onto the support 24, which then is in the "load" position, the cover is closed and its switch, via the CPU controller, directs the stepper drive motor 88 to rotate the carousel 20 to the "home" position, with the projection 54 to the rear of the MCL apparatus 10. The two sensors 100 and 106 control the rotative positioning movement of the carousel 20, as now will be described.

The Home Sensor Mechanism 106 consists of a fixed optical sensor 107 and a metal flag 104 attached to the carousel rotor shaft 60. The flag 104 passes through the optical sensor when the turntable is rotated. This causes the interruption of a light beam which in turn produces an electrical signal readable by the controller 282.

The Home Sensor Mechanism 106 is used to detect when the carousel 20 is at the "home" position. The carousel is turned by the stepper motor 88 until the "home" flag 104 blocks the "home" sensor 106. This sensor only provides approximate positioning, and is used to quickly move to the "home" position.

Between each tube position is a distance equivalent to thirty-two steps of the stepper drive motor 88; i.e. thirty-two motor pulses per each tube step to a next position. Thus, by pulsing the drive motor 88 thirty-two times, the carousel 20 moves one tube position. The Tube Positioning Mechanism 100 consists of an opaque plastic optical sensor disc 96 that has 33 slots placed evenly around its periphery. Each slot represents a tube (or "home") position. This disc is passed through an optical interrupter 103 which produces an electrical signal that directly correlates to the disc slot position within the sensor. The positioning disc 96 has very narrow slits 98 that, together with a narrow light beam produced by the optical interrupter 108, yields high rotational positioning precision and accuracy.

The Tube Positioning Sensor 100 is used to first arrive at an accurate "home" position, and then to check positioning accuracy after the stepper motor 88 rotates the carousel 20 to a desired location. In order to avoid tube damage or apparatus jams, the slits 98 are used to check to see that the carousel 20 has moved a tube 22 into a precise tube position, directly centered over the self centering lifter/vortexer mixer 28.

When the MCL apparatus 10 is powered up, assuming its cover its closed, a continuous, rapid stream or burst of pulses is applied to the stepper motor 88, rotating the carousel 20. The CPU controller 282 is signaled by the home position sensor 106 when it becomes blocked by the actuator flag 104 on the actuator member 102 as the carousel 20 is rotated. The signal from the sensor 106 causes the stepper motor 88 to then move more slowly, only one step at a time, until the tube position sensor 100 indicates a slit 98 has passed between its U-shaped arms. Once the leading edge of a slit 98 passes within the sensor 100, the stepper motor 88 is then commanded to look for the next slot edge, while keeping track of the number of pulses it took to get there. The controller 282 then knows the number of pulses necessary to traverse the slit. The total number of pulses are then divided by two (2), the controller 282 reverses the direction of rotation of the stepper motor 88, and steps the number of pulses calculated. This positions the carousel 20 in the center of the slit. All positioning references are then made from this point.

Once the carousel 20 has been positioned accurately at a "home" position, the MCL controller 282 issues pulses to the stepper motor 88 to advance to the next tube position, or a multiple of 32 pulses or steps. Proper positioning is checked with the Tube Positioning Mechanism 100. If a positioning error is not detected, the carousel 20 is rotated in the opposite direction by one half the distance between tubes. This operation is necessary to read the bar code 46 on the carousel 20 placed between tube positions. After a successful read, the direction of rotation is changed again and the carousel 20 is advanced back to its original tube position.

The carousel 20 is "re-homed" if a positioning error is detected. This is to attain the original position accuracy first achieved. The controller 282 then commands the stepper motor 88 to go to a desired tube position.

The tube position and home detect sensors 100 and 106 respectively, provide gross and fine positioning of the carousel 20, with respect to the home position and the position of the next tube 22 to be acted upon. The tube position detect sensor 100 indicates to the CPU controller 282 that the carousel 20 has rotated, from whatever position it was in when stopped, to a slit 98. If the carousel is not in the proper position precisely over the LV mixer 28 to raise a tube and mix its contents, the LV mixer up/down actuator solenoid 310 (FIGS. 2, 10) is not activated. This prevents the LV mixer from moving up, lifting a tube 22 out of the carousel 20 and possibly breaking the tube; thereby splashing outward the contents of the sample, which could be a hazard to the health of the operator. Additionally, this sensor is employed to align the tube to a correct or centered position. This is the reason for the slight adjustment provided for the sensor 100 by means of the previously described adjustment members 108 disposed along the side edge of the plate 74, located adjacent the disc 96.

This is the "home" reference position and so it must be accurately aligned.

Figure 3:
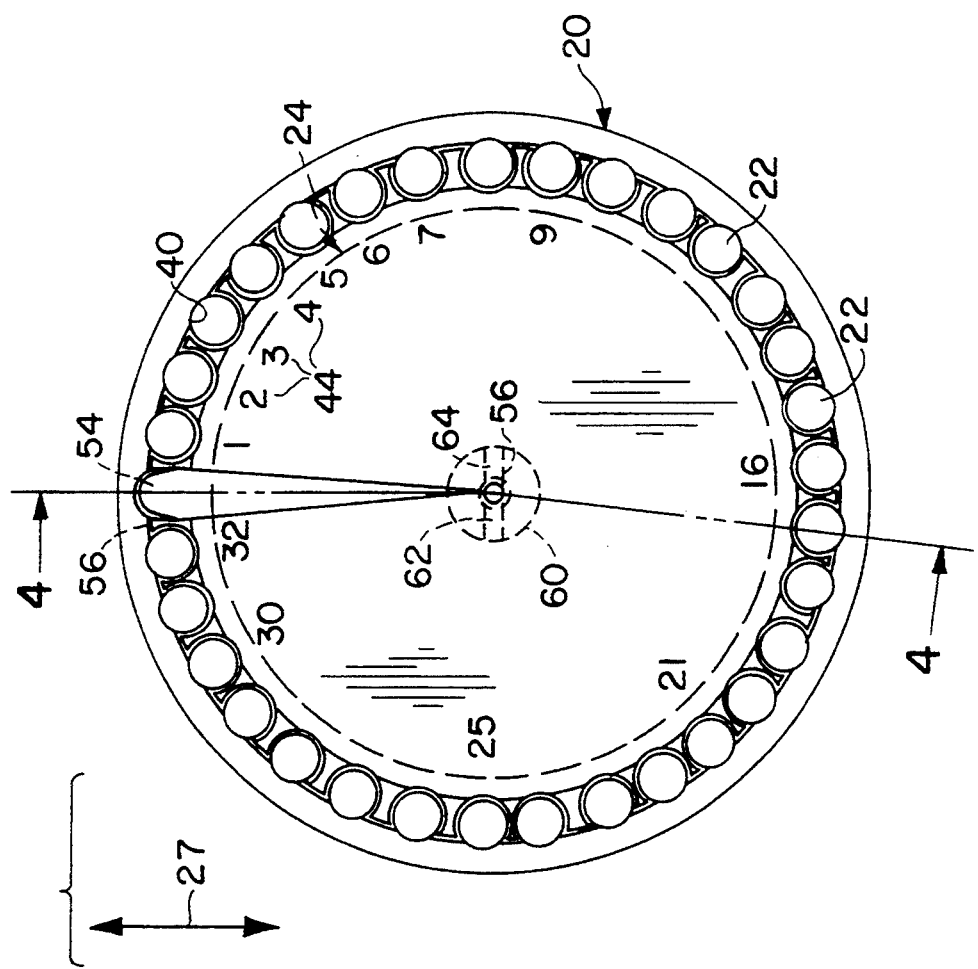
FIG. 3 is a top plan view of the sample holding carousel used with this invention.

It is understood that "home" position of the carousel is with the projection knob 54 of the carousel support aimed, as in FIG. 3, at the back of the apparatus (to the right in FIG. 2). However, the carousel is loaded onto the carousel support 24 with the projection 54 90° to the left of the home position. With the carousel 20 at the "home" position, the bar code reader/scanner 288 is aligned to read the carousel position bar code as well as the tube identification bar code indicated. This is also the home position of the first tube 22 of the group of tubes on the carousel. Thus, the home position is position zero "0".

Figure 11:
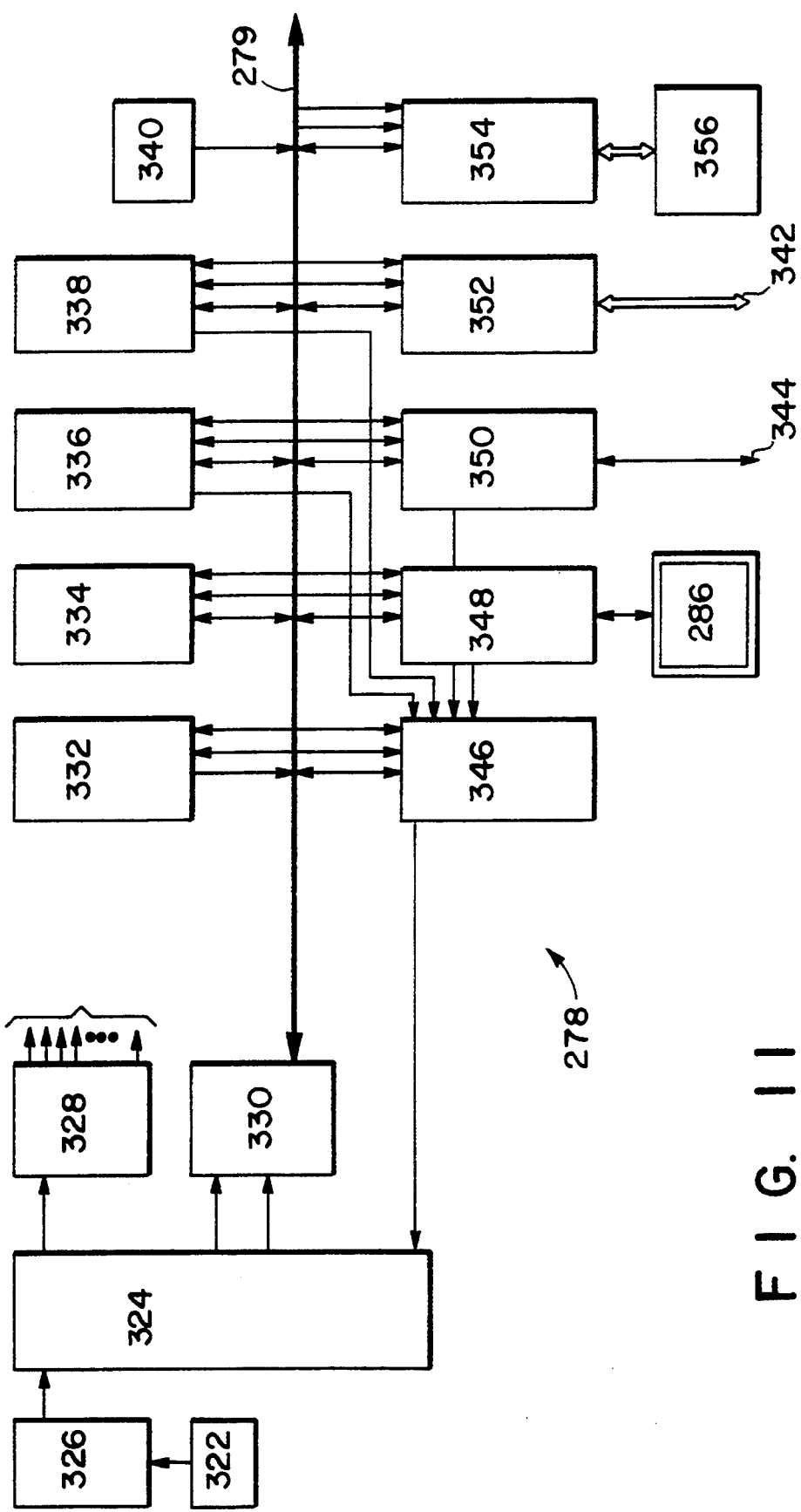

The present MCL apparatus 10 is adapted to operate automatically and in an unattended fashion. Control circuitry for each of the multiplicity of operations, as earlier briefly mentioned, is contained on printed circuit board members 278 and 280, (FIGS. 2 and 10). The circuit board 278 supports a CPU controller 282, which controls the mechanical assembly 11 (FIG. 1). The entire content of FIG. 11 is contained in the dotted outline Box 278 of FIG. 10. All of the components above the bus 279, FIG. 11 are contained in the Box 292 of FIG. 10. A 24 VDC power source 293 is used to "power up" the electrical circuitry 278. The circuit board 280 contains the bar code reader electronic control circuitry 284 for a bar code reader 286, including a bar code reader/scanner (not shown). Indicators 290 and buttons 292 are located on the operably associated flow cytometer 19.

A parallel I/O interface 294 is located on the printed circuit board 278 and its electrical input signals come from the flow cytometer 19. This interface provides access from the flow cytometer to the CPU controller 282. A scanner relay 296 and a scanner power input 298 operate with the interlock detect 300 to automatically turn "off" the bar code reader/scanner (not shown), to prevent laser beam emission, which if unchecked could cause personnel injury.

The interlock detect 300 also indicates the status of the sample tube support head 32 and sample aspirating member 34, which must be in operative position for the apparatus 10 to operate. The scanner power input 298 energizes the bar code scanner/reader (not shown) from a serial interface connector 302 on 278. The cover interlock detect 304 includes switches which are wired in series, such that if one switch fails the other will trip and shut off the power.

The probe detect chip 262, the head detect chip 250, the LV up/down detect chip 240 and the carousel in/out detect chip 294 all refer to previously described mechanical apparatus illustrated in FIG. 9. These detectors indicate the status of each moveable part of the apparatus 10. For example, if the sample probe 34 should become stuck in a half way up position, this is considered a fault, and appropriate technician action is required.

The sample head detect sensor 226 primarily detects that a tube 22 has been loaded. Its secondary function is operative during any scanning sequence or tube loading routine, when the sample probe 214 is aspirating, such that if the tube 22 should break or should be flung out of the carousel 20, this sensor 226 will instantly shut down the total operation. The flow cytometer then will "ask" for a status report and the MCL 10 will "report" the detect sensor head fault.

The LV up/down detect sensor 224 is the tube position monitor. This detector indicates that the tube sensor actuator or flag 242 reached a certain raised position at a predetermined time monitored by the software program. The software assembly 17 keeps track of the time and the status of this sensor 224.

The carousel in/out detect sensor 230 (FIG. 5) detects the horizontal position (arrow 27) of the carousel 20 with respect to the self centering lifter vortexer/mixer 28. If the carousel 20 is not in the proper position for the vortexer mixer 28 to raise a tube 22 from the carousel 20 and mix the tube contents, the vortexer/mixer is not activated.

Four solenoid operated valves, identified as: carousel in/out actuator solenoid 306, sample probe actuator solenoid 308, LV up/down mixer solenoid 310, and sample tube rotator solenoid 312 are shown at the lower left in FIG. 2. The stepper motor 88 is controlled through a power driver 314 and motor control circuitry 316. The LV motor 128, which actuates the lifter vortexer/mixer 28, is controlled by the motor driver circuitry 318. A serial interface 320 provides the interconnection for an unused auxiliary serial port.

Referring now to FIG. 11, there is shown a reset block or chip 322, which detects when the supply voltage drops below a fixed, pre-programmed level. If the voltage does thus drop, the reset chip 322 resets the status of the whole circuit board 278. This action avoids any erroneous conditions or uncertain logic levels which might be caused by low supply voltage (from source 293 FIG. 10) solely during "power up". If the block 322 is not reset, this indicates to an MPU processor 324 that the electronic circuitry is at the proper voltage level so that the MPU processor 324 can execute commands accurately and in an ordered sequence. A clock chip 326 provides a clock frequency for microprocessor support, in well known fashion. An address decoder 328, which can be a PAL, is configured to have a linear addressing function. Address and data latches 330 provide additional addressing access to memory. An E prom 332 and two 32K RAM chips 334 and 336 provide the current capability for the electrical assembly 13.

In FIG. 11, the multiple output lines from the address decoder 328 provide means to address many locations in the processor board system. The electrical assembly 13 must be given a specific command instruction to access a specific address therein. The two RAM chips 334 and 336 introduce various operational states into and out of the MCL apparatus 10 during operation. A timer 338 is operationally based on the cycle of the clock 326, to provide an accurate time base to run certain time sequences used in the electrical control assembly 13.

Configuration switches 340 are a plurality of LED/dip switches used to set the MCL apparatus 10 into its various modes of operation. For example, by appropriate configuration switch setting, the MCL apparatus 10 can take its commands solely from the flow cytometer 19; or it can be operated from a lap top computer (not shown) for test purposes or diagnostic routines. Command inputs solely from the flow cytometer 19 are through a parallel control interface line 342. Other type of command inputs can be introduced via a serial control interface line 344.

An interrupt controller 346 monitors other event/signals entering inputs from other ports of the circuit board 278. These signals can come from inside or outside the MCL apparatus 10, or from other switches. The main purpose of this chip 346 is to locate the interrupt, whatever or wherever it is, and to inform the electrical assembly, so that appropriate rectifying action can be taken in an orderly fashion. Two serial I/O's 348 and 350 are located in interfaces 302 and 320 and perform dedicated functions. The serial I/O 348 is completely dedicated to the bar code reader scanner 286; all communications to the scanner go through this port 348. The second I/O 350 is connected to the serial control interface line 344, for future use.

A first parallel I/O 352 is connected and configured to provide inputs to the parallel control interface line 342. This I/O interfaces with any of the many switches used throughout the electrical assembly 13. This I/O accepts all of the input data and is dedicated to the flow cytometer 19. The second parallel I/O 354 interfaces with buffer and driver circuits 356. The flow cytometer 19 has all of its communications with the MCL apparatus 10 through the I/O 354.

Description of an Operational Cycle of the MCL Apparatus 10

As is typical in the use of flow cytometry, the human operator pre-programs the cytometer 19 via the work station 15 to set up a protocol for conducting one or more tests upon a sample, for example from a tube 22. Since the present invention and its example of the carousel 20 can hold up to thirty-two sample tubes, the human operator can pre-program the work protocol or program to be done on any and/or all of the samples on the carousel soon to be loaded into the MCL apparatus 10. Essential to the operator input protocol is designation of the bar code indicia label 42 of the sample tube upon which certain specific tests are to be conducted and its pocket position 46 in the carousel. Also, if more than one carousel is to be employed, its designator is to be inputted into the protocol. The protocol can be input prior to or after the carousel is mounted onto the stub shaft 60 on the plate 74. Then the MCL 10 apparatus cover is closed, so that the MCL can enable total automatic system operation.

With the flow cytometer 19 "ON", the MCL apparatus 10 automatically is energized. There are a number of initialization procedures and processes that take place automatically. The apparatus 10 resets the CPU controller 282 to ensure that it is in the proper state to begin operation. The apparatus 10 now is in an idling condition waiting for commands. The flow cytometer 19 has checked all its sensors, all processors, etc. and has initiated a software reset. The MPU processor 324 of the MCL 10 initiates a reset of the scanner board 286 and simultaneously starts putting all the mechanisms of the mechanical assembly 11 in their proper positions. The carousel support 24 is moved outward (arrow 27) into the "load" position, which is the standard position for loading and unloading the carousel 20 carrying its tubes 22. The apparatus 10 now waits for the next command from the flow cytometer 19. At this point, the flow cytometer 19 can send a tube load command and designate which tube, by number, is to be loaded.

Assuming at this point that the carousel is loaded into the apparatus and the cover of the apparatus 10 is closed, the operator presses an "auto" start button on the flow cytometer 19. The cytometer 19 now sends the tube load command to the MCL apparatus 10. The carousel 20 turns around counter clockwise. First, the carousel position 44 is identified, then the carousel number is read for identifying the proper carousel 20, and then the number 42 tube 22 to be tested is identified. The carousel now is moved forwardly or "in" to the proper tube position and the tube is centered. The finger 30 extends outwardly and oscillates back and forth against the side of the tube, rotating the tube circularly. During this rotating portion of the cycle, the bar code reader 286 reads the bar code label 42 on the tube, identifying the specific tube for a specific test. The bar code reader electronic control circuitry 284 is preprogrammed to provide a number of reads. When it has produced three so-called "good reads", the reader circuitry 284 indicates a valid read. This identifies the information/data on the tube. This data is then fed back to the flow cytometer 19, where a system check of the data then is made. The tube 22 is still in pocket 40 in the carousel 20 at this point. This ends the tube load command.

The flow cytometer 19 now issues a "tube raise command". The finger 30 comes out again and this time the finger 30 is utilized as a support device for the tube 22. As the tube 22 is lifted from the carousel 20 (pushed upward from the pocket 40) by the lifter vortexer 28, the finger 30 prevents the tube from tilting or wobbling out of the vertical orientation. The lift command is sent to the LV up/down actuator solenoid 310, which then raises the tube 22 to engage the open top of the tube with the sample tube support head 32. The distance the tube travels during the "up" excursion depends upon the length of the tube. The LV up/down vortexer 28 now is actuated to rotate the tube. The motor driver 318 switch is turned "on" and the motor 128 causes the LV mixer 28 to rotate the tube 22 and resuspend or mix its contents. When the mixing is completed, the probe actuator solenoid 308 is energized, bringing the elongated probe 214 down into the tube. The probe detect 262 is operable to indicate the position of the probe 214 with respect to the sample head 32. The tip of the probe 214 enters the tube 22 and goes almost to the bottom of the tube. The tube now is pressurized by compressed air, which enters the tube via the orifice or passageway 192 in the sample head 32. The air forces a specific volume of fluid sample vertically upwardly through the probe 214 into the flow cytometer 19 during a predetermined time sequence. Then, applied vacuum to the orifice or passageway 194 sucks up any refuse or liquid drops that remain on the probe 214. The sample tube support head 32 and the probe tip are washed by fluid which is introduced via the pressure passageway 192 and simultaneously the wash and waste fluids are sucked out via the vacuum passageway 194, thus cleaning that portion of the apparatus. Next, the probe 214 is lifted vertically upward to its fully retracted position. The tube 22 is lowered by the LV vortexer mixer 28 and the sample head 32, which is spring biased upwardly by the spring 212, is forced up into a retracted home position. If the tube 22 happens to stick within the sample head 32, there is a "shake" command through the motor control 316, whereby the tube 22 is now shaken or vibrated prior to being returned to the carousel pocket from which it came. At this point, the apparatus 10 waits for another command from the flow cytometer 19. The cycle of operation is completed and the carousel 20 moves outwardly and rotates to the load position. The MCL apparatus 10 now waits for the next operational command.

We claim:

1. Apparatus for automatically and selectively transferring multiple, randomly associated hematological samples from a group of samples to an operably associated cytometric apparatus comprising, at least one sample container, each containing a preselected, individually identifiable hematological sample, sample container carrier means for moving said sample containers on a path of movement including means for supporting a plurality of sample containers thereon, movable sample receiving means for pressurizing said sample prior to passing said sample to a cytometric apparatus, means for moving said sample container carrier means normal to the path of movement of said sample receiving means, sample resuspending and mixing means operably associated with said sample container carrier means for automatically removing a sample container from said carrier means and engaging said sample container with said sample receiving means, so that activation of said sample resuspending and mixing means resuspends and mixes said sample, a movable member having means for contacting said sample container and vertically lifting said container from said carrier means into temporary sealing engagement of said sample container with said sample receiving means and for translating the vertical lifting movement into circular, vortexing movement so as to vortex the contents of said sample container, said movable member including a vertically disposed member having a slidable counter balance affixed at one end, permitting said movable member to automatically adjust its position from off-center to center as it is moved with respect to a sample container, said sample container carrier means including an opening in said supporting means below each sample container and said movable member contacting means moves through said opening to lift said container from said carrier means, and aspirating means operably engagable with said sample receiving means for delivering said sample from said sample container to said cytometric apparatus in response to the pressurizing of said sample.

2. The apparatus in accordance with claim 1 wherein said sample container carrier includes preselected identification indicia to identify each individual sample container.

3. The apparatus in accordance with claim 1 wherein said sample container carrier means includes a demountable, rotatable carousel including drive engaging means for engaging carousel and said container carrier means.

4. The apparatus in accordance with claim 3, further including drive means for coupling to said drive engaging means and orienting means for orienting said carousel in load and home positions.

5. The apparatus in accordance with claim 4 wherein said orienting means includes position and indicating means for rotating said sample container carrier means to move a selected sample container into engagement with said sample resuspending means and for moving said selected sample container into engagement with said sample receiving means.

6. The apparatus in accordance with claim 1 wherein said sample receiving means includes integral back flushing means for removing residual sample therefrom.

7. The apparatus in accordance with claim 1 further including means horizontally movable into and out of engagement with a sample container for automatically rotating said sample container into a position for identifying individual indicia thereon and for supporting said sample container when said sample container is removed from said carrier means for engagement with said sample receiving means.

8. The apparatus in accordance with claim 7 wherein said means for rotating and supporting said sample container comprises an elongated, pivoted link carrying a resilient sample container engaging member at a free end thereof.

9. The apparatus in accordance with claim 1 further including drive means for moving said movable member vertically up and down.

10. The apparatus in accordance with claim 1 including signal generating means for indicating the position of said container carrier means with respect to said movable member so as to coaxially position said movable member beneath a sample container, enabling said sample container to be raised vertically clear of said carrier means to bring said sample container into sealing engagement with said sample receiving means.

11. The apparatus in accordance with claim 1 wherein an individual electro-optical position sensor is operably associated with each one of said container carrier means, said sample receiving means, said sample resuspending and mixing means and said aspirating means; each of said position sensors including an elongated opaque member operably positioned to interrupt and activate a respective sensing member as said carrier means, said sample receiving means, said sample resuspending and mixing means and said aspirating means is moved during operation of said apparatus.

12. An apparatus for selectively transferring samples from a group of samples, comprising:

a plurality of sample containers, each container including a base end and a sample loading and aspiration end;

a sample carrier including means for holding at least said base end of said plurality of sample containers and means for moving said sample containers to a mixing station;

means for supporting said sample loading and aspiration end of said sample containers in said aspiration location spaced from said sample carrier;

sample resuspending and mixing means operably associated with said sample container carrier for removing a sample container from said carrier means and engaging said sample container with said supporting means, so that activation of said sample resuspending and mixing means resuspends and mixes said sample, a movable member having means for contacting said sample container and vertically lifting said container from said carrier into temporary sealing engagement of said sample container with said supporting means and for translating the vertical lifting movement into circular, vortexing movement so as to vortex the contents of said sample container, said movable member including a vertically disposed member having a slidable counter balance affixed at one end, permitting said movable member to automatically adjust its position from off-center to center as it is moved with respect to a sample container, and said sample container carrier including an opening in said base end holding means below each sample container and said movable member contacting means moves through said opening to lift said container from said carrier.

13. The apparatus in accordance with claim 12 including aspirating means operably engagable with said supporting means for delivering said sample from said sample container.

* * * * *